United States Patent
Daddona et al.

[11] Patent Number: 6,091,975
[45] Date of Patent: Jul. 18, 2000

[54] MINIMALLY INVASIVE DETECTING DEVICE

[75] Inventors: Peter E. Daddona, Menlo Park; Gregory T. Fieldson, Palo Alto; Avtar S. Nat, Fremont; Wei-Qi Lin, Palo Alto, all of Calif.

[73] Assignee: Alza Corporation, Mountain View, Calif.

[21] Appl. No.: 09/053,272

[22] Filed: Apr. 1, 1998

[51] Int. Cl.⁷ .................................................. A61B 5/05
[52] U.S. Cl. ...................... 600/345; 600/309; 600/347; 600/365; 600/373
[58] Field of Search ........................... 600/345, 346, 600/347, 348, 354, 357, 366, 382, 384, 386, 393, 372, 309, 365, 373

[56] References Cited

U.S. PATENT DOCUMENTS

| | | | |
|---|---|---|---|
| 3,505,993 | 4/1970 | Lewes et al. | 128/2.06 |
| 3,675,766 | 7/1972 | Rosenthal | 206/63.7 |
| 3,814,097 | 6/1974 | Ganderton | 128/268 |
| 3,964,482 | 6/1976 | Gerstel et al. | 128/260 |
| 4,120,292 | 10/1978 | LeBlanc, Jr. et al. | 128/2 E |
| 4,195,641 | 4/1980 | Joines et al. | 128/632 |
| 4,294,258 | 10/1981 | Bernard | 128/635 |
| 4,344,440 | 8/1982 | Aaby et al. | 128/653 |
| 4,539,994 | 9/1985 | Baumbach et al. | 128/635 |
| 4,685,465 | 8/1987 | Klitgaard et al. | 128/635 |
| 4,685,466 | 8/1987 | Rau | 600/387 |
| 4,703,756 | 11/1987 | Gough et al. | 123/635 |
| 4,711,247 | 12/1987 | Fishman | 128/743 |
| 4,756,314 | 7/1988 | Eckenhoff et al. | 128/760 |
| 4,759,374 | 7/1988 | Kierney et al. | 128/663 |
| 4,825,879 | 5/1989 | Tan et al. | 128/633 |
| 4,830,014 | 5/1989 | Goodman et al. | 128/665 |
| 4,836,907 | 6/1989 | Pedersen | 204/412 |
| 4,844,098 | 7/1989 | Mitchen | 128/765 |
| 4,926,867 | 5/1990 | Kanda et al. | 128/633 |
| 4,953,552 | 9/1990 | DeMarzo | 128/635 |
| 4,969,468 | 11/1990 | Byers et al. | 600/373 |
| 5,029,583 | 7/1991 | Meserol et al. | 128/633 |
| 5,036,861 | 8/1991 | Sembrowich et al. | 128/763 |
| 5,108,819 | 4/1992 | Heller et al. | 428/195 |
| 5,140,985 | 8/1992 | Schroeder et al. | 128/632 |
| 5,197,471 | 3/1993 | Otero | 128/640 |
| 5,203,327 | 4/1993 | Schoendorfer et al. | 128/632 |
| 5,208,154 | 5/1993 | Weaver et al. | 435/176 |
| 5,220,919 | 6/1993 | Phillips et al. | 128/632 |
| 5,267,563 | 12/1993 | Swedlow et al. | 128/633 |
| 5,279,544 | 1/1994 | Gross et al. | 604/20 |
| 5,285,783 | 2/1994 | Secker | 128/633 |
| 5,313,940 | 5/1994 | Fuse et al. | 128/633 |
| 5,345,935 | 9/1994 | Hirsch et al. | 128/642 |
| 5,390,671 | 2/1995 | Lord et al. | 600/347 |

(List continued on next page.)

FOREIGN PATENT DOCUMENTS

| | | | |
|---|---|---|---|
| 0 353 328 A1 | 2/1990 | European Pat. Off. | A61B 5/00 |
| 25 06 175 A1 | 8/1976 | Germany | A61B 5/00 |
| 37 13846 A1 | 4/1988 | Germany | A61B 5/14 |
| WO 89/02720 | 4/1989 | WIPO | A61B 5/00 |
| WO 96/37155 | 11/1996 | WIPO | A61B 17/20 |
| WO 96/37256 | 11/1996 | WIPO | A61N 1/30 |
| WO 97/07734 | 3/1997 | WIPO | A61B 5/00 |

OTHER PUBLICATIONS

Reiss, Susan M., Biophotonics International, May/Jun. 1997, pp. 43–45, "Glucose– and Blood–Monitoring Systems vie for Top Spot".

Eppstein, Jonathan, et al., "Rapid Transdermal Drug Delivery with Thermal Micro–Poration", Dec. 12, 1997 Presented at transdermal conference sponsored by IBC from Dec. 15–Dec. 18, 1997 in San Diego, Ca.

*Primary Examiner*—Cary O'Connor
*Assistant Examiner*—Navin Natnithithadha
*Attorney, Agent, or Firm*—D. Byron Miller; Steve F. Stone

[57] ABSTRACT

An agent detecting device comprising a plate (6) having a plurality of microprotrusions (4) for piercing the skin of a patient. Each of the microprotrusions (4) having an electrode (14, 16 and 18) thereon for detecting the presence of an agent in the patient's interstitial fluid.

29 Claims, 2 Drawing Sheets

U.S. PATENT DOCUMENTS

| | | | |
|---|---|---|---|
| 5,391,250 | 2/1995 | Cheney, II et al. | 156/268 |
| 5,402,777 | 4/1995 | Warring et al. | 604/307 |
| 5,425,868 | 6/1995 | Pedersen | 204/408 |
| 5,445,147 | 8/1995 | Schoendorfer et al. | 128/632 |
| 5,452,717 | 9/1995 | Branigan et al. | 128/633 |
| 5,482,034 | 1/1996 | Lewis et al. | 128/633 |
| 5,497,769 | 3/1996 | Gratton et al. | 128/664 |
| 5,535,744 | 7/1996 | DiNino | 128/635 |
| 5,600,134 | 2/1997 | Noller | 23/232 | ical sensors to individual skin-piercing elements rather than in close parallel relation on one sensor probe for improved manufacturability.

MINIMALLY INVASIVE DETECTING DEVICE

TECHNICAL FIELD

The present invention relates to percutaneous detecting devices. More particularly, this invention relates to percutaneous detecting of agents, such as body electrolytes, glucose, alcohol, pharmaceuticals and illicit drugs using transcutaneous sensors.

BACKGROUND ART

Interest in the percutaneous detecting of body analytes (i.e., fluid electrolytes), organics (e.g., glucose), pharmaceuticals and illicit drugs has grown over the years. In recent years, a number of electrochemical sensors have been developed for detecting each of these analytes in the blood or interstitial fluid of a patient. For example, glucose sensors have been developed for obtaining an indication of blood glucose levels in diabetic patients. Existing electrochemical sensors require either collection of a sample from the patient or some form of invasive insertion of a sensor probe into the patient.

Thin film electrochemical sensors have been developed for subcutaneous placement of sensor probes in direct contact with the patient's blood or other extracellular fluid. One such example of a thin film electrochemical sensor, disclosed in U.S. Pat. No. 5,391,250 issued to Cheney, II et al., is fabricated using thin film mask techniques. With thin film mask techniques, three thin film conductive elements are laid down in close parallel relation on a substrate and encased between flexible insulating layers of polyimide material. The conductive elements are left exposed at the distal end of the electrochemical sensor for placement in direct contact with the patient's blood. Appropriate electrode chemistries are applied to the exposed conductive elements for use as a blood glucose sensor. One of the exposed conductive elements has a coating containing glucose oxidase to define a working electrode. The other two exposed conductive elements are coated with other suitable materials or left uncoated to define a reference electrode and a counter electrode for the electrochemical sensor. The conductive elements are left exposed at the externally located proximal end for connection to a suitable monitor.

The exposed conductive elements at the distal end of the electrochemical sensor are transcutaneously placed using a sensor insertion set such as disclosed in U.S. Pat. No. 5,390,671 issued to Lord et al. The sensor insertion set comprises a separate slotted insertion needle extending through a mounting base that attaches onto the patient's skin. The thin film sensor has a proximal end carried by the mounting base and a distal segment with the exposed sensor electrodes thereon protruding from the mounting base. The proximal end of the sensor is linearly offset from the distal segment so that the distal segment can be fitted into the slotted insertion needle while the proximal end is carried by the mounting base. The distal segment is transcutaneously placed as the insertion needle pierces the patient's skin upon the mounting base being pressed onto the patient's skin. The insertion needle is then withdrawn over the electrode from the patient leaving the distal segment at the selected site and the mounting base on the patient's skin.

Insertion of the needle is comparatively invasive, painful and frightening to many patients. Therefore, there is a need for a minimally invasive, painless placement of electrochemical sensors in the patient's skin. Furthermore, it is desirable in some circumstances to apply the electrochemical sensors to individual skin-piercing elements rather than in close parallel relation on one sensor probe for improved manufacturability.

DESCRIPTION OF THE INVENTION

The present invention is a detecting device and method for placing an electrochemical sensor in contact with a patient's interstitial fluid with skin piercing microprotrusions in a minimally invasive manner. The device of the present invention pierces the stratum corneum of a body surface to position the electrochemical sensor just below the outermost layer of the epidermis but above the patient's nerve endings and blood vessels to eliminate pain and bleeding for the patient. The present invention integrates an electrochemical sensor and at least one skin-piercing member into one device to achieve in situ detection with a painless application.

In one aspect, the invention comprises a plurality of microprotrusions for piercing the skin in which each microprotrusion forms an individual electrode of an electrochemical sensor, instead of all of the electrodes on one probe, to maximize the electrode area while maintaining the small protrusion size necessary for minimally invasive operation. In another aspect, the electrodes are coated onto each side of the microprotrusions to increase the active electrode area.

In another aspect of the invention, the device utilizes a member having an opening therethrough in communication with a fluid-attracting member, a plurality of microprotrusions extending downward from a first side of the member, and a thin-film electrode on the microprotrusions which form an electrochemical sensor. With the thin-film electrodes inserted in the patient's skin, a constant flow of interstitial fluid past the electrodes can be maintained by drawing the fluid through the opening with the fluid-attracting member (e.g., an osmotic salt layer).

MODES FOR CARRYING OUT THE INVENTION

Figure 1:
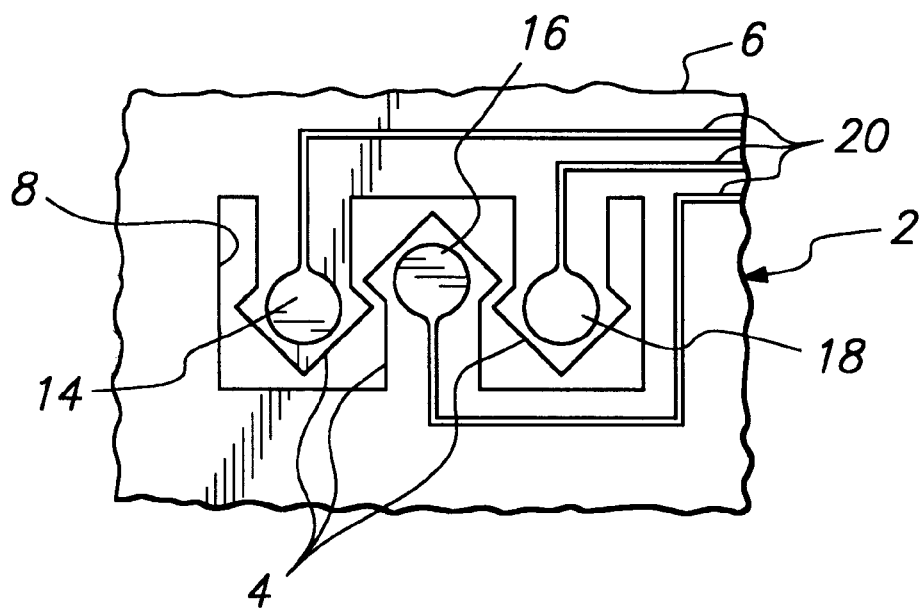
FIG. 1 is a top plan view of a portion of a member with microprotrusions having sensor electrodes thereon.
Figure 2:
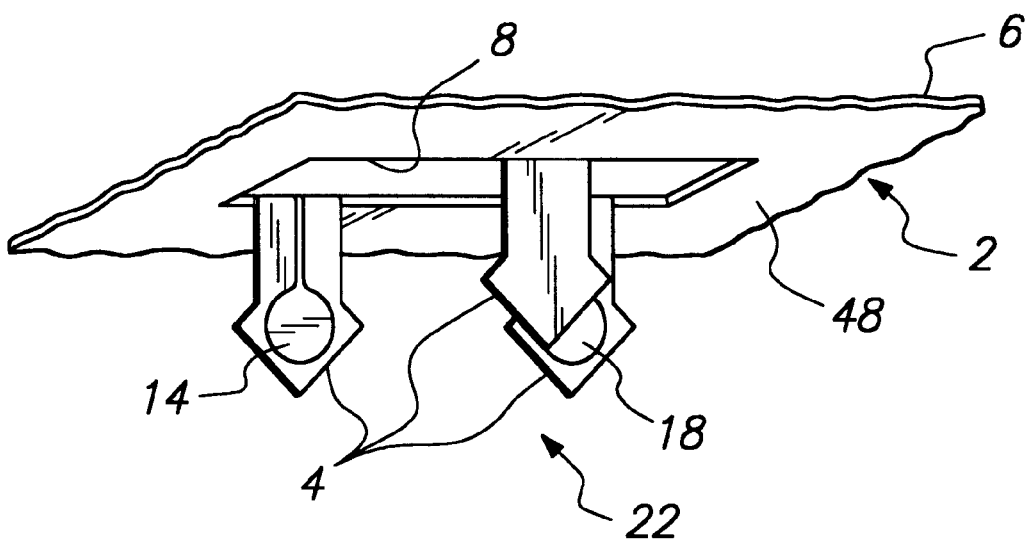
FIG. 2 is a bottom perspective view of the member of FIG. 1 after the microprotrusions have been bent into position.

Turning now to the drawings in detail, one embodiment of the skin piercing member 2 of the present invention is generally shown in FIGS. 1 and 2. Member 2 is used for the percutaneous detecting of an agent. The term "detecting" is used broadly herein to include detection of or sensing the presence or amount of an agent, as well as monitoring the presence or amount of an agent. The terms "substance", "agent" and "drug" are used interchangeably herein and broadly include substances such as glucose, body electrolytes, alcohol, illicit drugs, pharmaceuticals, etc. that can be sampled through the skin. The major barrier properties of the skin, such as resistance to agent detecting, reside with the outer most layer (i.e., stratum corneum). The inner division of the epidermis generally comprises three layers commonly identified as stratum granulosum, stratum malpighii, and stratum germinativum. There is essentially little or no resistance to movement of an agent through the stratum granulosum, stratum malpighii, and stratum germinativum. The device of the present invention is used to pierce the stratum corneum 24 for in situ detecting of an agent with a sensor located below the outermost layer of the patient's skin (FIG. 3).

Figure 4:
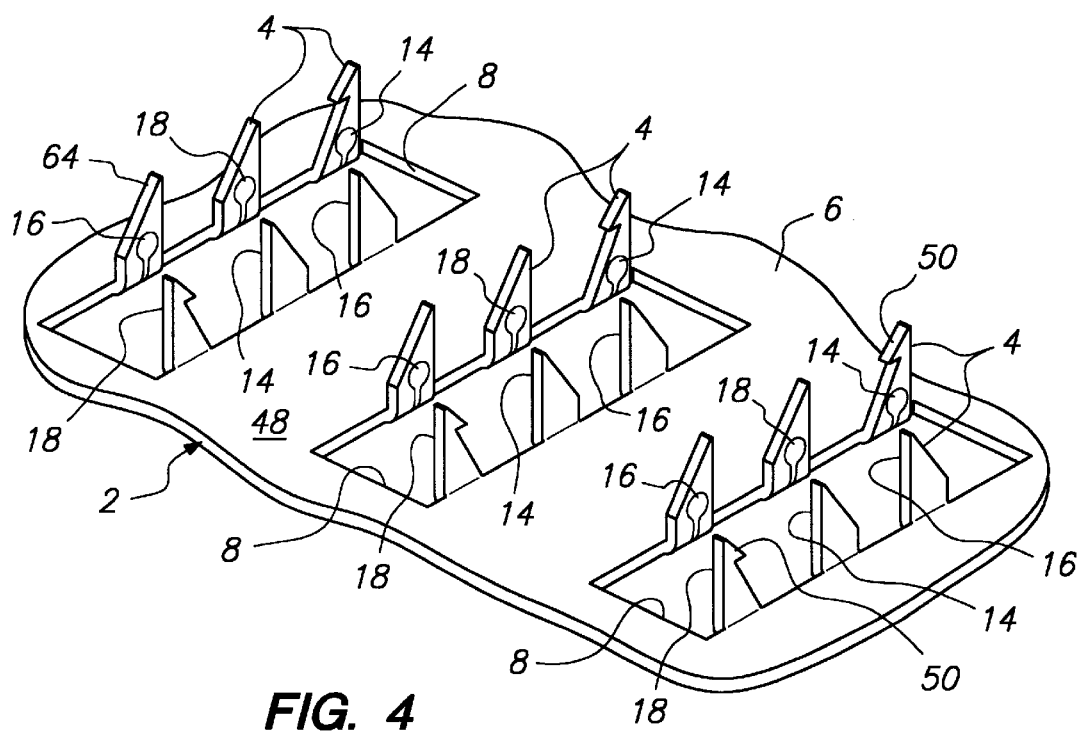
FIG. 4 is an enlarged perspective view of the bottom side of a member in accordance with another embodiment of the present invention.

Member 2 comprises a plurality of microprotrusions 4 which are sized and shaped for piercing the outermost stratum corneum layer of (e.g., human or other animal) skin. FIG. 1 shows the microprotrusions 4 after they are formed (by a photolithography process followed by a chemical etching process described in more detail hereinafter) and after coating (e.g., by printing) electrodes 14, 16, 18 and electrical traces 20 thereon. FIG. 2 shows the microprotrusions 4 after they have been bent to extend (e.g., perpendicularly) downward from the plane of plate 6. FIG. 4 shows member 2 in an inverted position to better show the microprotrusions 4. Only a portion of the plate 6 is shown in FIGS. 1, 2 and 4. The member 2 provides for the transcutaneous placement of a flexible sensor 22 having one or more electrodes at a selected site within the body of a patient. Particularly member 2 facilitates the placement of a flexible thin film electrochemical sensor of the type used for detecting specific parameters representative of patient conditions. Placing the sensor within the skin of the patient allows in situ readings to be obtained instead of relying on collecting interstitial fluid into an absorbing member. The in situ detection minimizes lag time in the readings compared to diagnostic methods which rely on extracting the interstitial fluid before the measurement can take place. In one preferred embodiment, the sensor is designed to monitor glucose levels in diabetic patients.

In the embodiment illustrated in FIGS. 1 and 2, the member 2 comprises a three electrode electrochemical sensor shown generally at 22 having a sample electrode 14, common electrode 16 and reference electrode 18. Electrical traces 20 are routed from each electrode along the upper surface of the device 2 for interface with an electronic control unit or detector 10 (shown schematically in FIG. 3). The three electrodes 14, 16 and 18 on the adjacent microprotrusions 4 are moved into the orientation shown in FIG. 2 by placing the plate 6 of FIG. 1 on a die (not shown) and using a punch (not shown) which is pushed through the opening 8. The microprotrusions 4 of the electrochemical sensor 22 are sized appropriately so that they reach through the stratum corneum 24 but do not contact the patient's nerve endings 26 (FIG. 3). For example, the tear drop shaped electrodes 14, 16 and 18 shown in FIGS. 1 and 2 at the tip of each microprotrusion 4 are about 100 micrometers in diameter and the microprotrusions 4 have an overall length of about 150 micrometers. With this configuration, electrochemical sensor 22 is responsive to changes in the presence or amount of agent in the patient's interstitial fluid without causing a painful sensation or bleeding. Prior to punching, the sensor 22 can be constructed using thin film mask techniques utilizing thin film conductors 20 embedded or encased between layers of selected insulated material such as polyimide film. The electrodes 14, 16 and 18 at the distal tip of each microprotrusion are inserted into the patient's skin in order to contact the patient's interstitial fluid when the sensor is transcutaneously placed.

Figure 3:
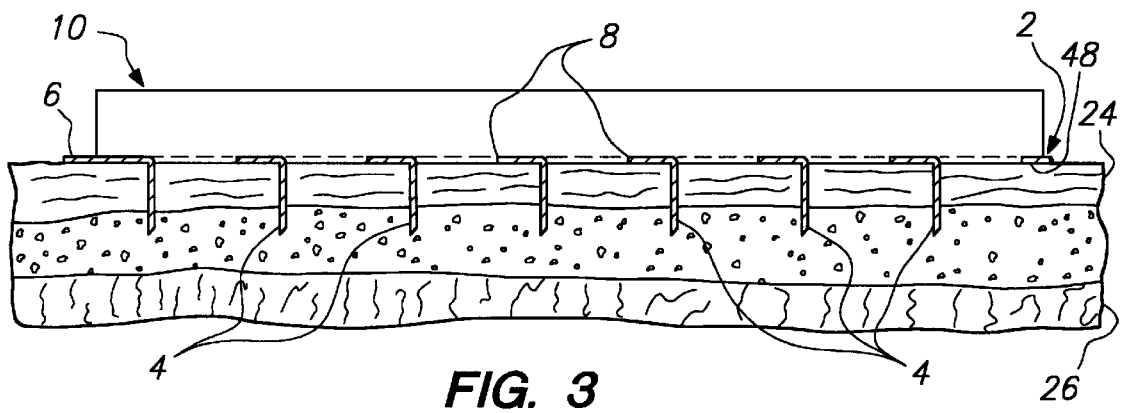
FIG. 3 is an enlarged partial cross-sectional view of a detecting device in accordance with the present invention.

As is known in the art and illustrated diagrammatically in FIG. 3, the diamond electrodes 14, 16 and 18 are in electrical communication, through conductive traces 20, with a suitable control unit 10 for detecting the patient's condition (e.g., blood glucose concentration) in response to signals derived from the sensor electrodes. Any suitable thin film mask techniques including with reference to those disclosed in U.S. Pat. No. 5,391,250 issued Feb. 21, 1995 to Cheney, II et al. and U.S. Pat. No. 5,108,819 issued Apr. 28, 1992 to Heller et al. can be used in the present invention. The sensor can be used over a prolonged period of time for periodically or continuously detecting a body electrolyte, such as glucose in a diabetic patient. Such readings are useful in monitoring the patient's blood glucose concentration (i.e., through appropriate software which correlates the concentration of glucose in interstitial fluid with the concentration of glucose in the blood) and can further be used to adjust a treatment regime which typically includes administration of insulin to the patient and/or appropriate modification of diet and/or exercise.

In the illustrative sensor construction shown in FIGS. 1 and 2 designed for use as a subcutaneous glucose sensor, each sensor 22 is shown to include three parallel conductors or traces 20 corresponding with three separate electrodes 14, 16 and 18. Appropriate electrode chemistries defining the tear drop-shaped electrode surfaces at the distal ends of the microprotrusions 4 can be applied as appropriate. In this illustrative sensor embodiment for use as a glucose sensor, electrode 14 includes glucose oxidase to define a working or sample electrode. The other two electrodes, counter electrode 16 and reference electrode 18 may contain other suitable chemistries, to define a counter electrode and a reference electrode for the electrochemical sensor 22. As is known to those skilled in the art of electrochemical analyte (e.g., glucose) sampling, at least the working electrode 14 should be coated with an excluding membrane in order to limit electrical interference due to oxidation or reduction of extraneous species in the interstitial fluid. The excluding membrane can be comprised of two layers, including a first layer for keeping scar tissue or macrophages from coating the electrode and reducing the active electrode area, and a second layer for excluding small molecular weight oxidizable or reducible species. In glucose sensing, the second layer is typically formed of cellulose acetate and is permeable to hydrogen peroxide but substantially less permeable to other endogenous oxidizable/reducible species.

The reference electrode is typically formed of silver/silver chloride and preferably contains an electrolyte having a controlled composition as is known to those skilled in the electrochemical sensing arts.

By placing each of the electrodes 14, 16 and 18 on a separate microprotrusion 4, instead of locating all of the electrodes 14, 16 and 18 on a single microprotrusion 4, the electrode area is maximized while maintaining a relatively small protrusion size necessary for a minimally invasive device.

In an alternate embodiment, the electrodes are coated onto each side of the microprotrusions doubling the active electrode area. The separation of electrodes on individual microprotrusions eliminates problems that are associated with depositing the reference, sample and common electrodes close together in a small configuration. The etched space between the electrodes guarantees safe separation of the electrode coating materials so that there is little chance of bleeding of one coating to another electrode during manufacturing. It is within the scope of the invention, however, to utilize only a single microprotrusion 4 with all of the electrodes 14, 16 and 18 on that one microprotrusion. Likewise, although a glucose sensor has been described, any detecting system can be utilized with the device 2. It is within the scope of the invention that the particular detecting system may have only one or two electrodes or may have more than three electrodes. If additional electrodes are needed for the detecting system, more microprotrusions can be used and arranged for the best configuration. The configuration illustrated in FIG. 4 utilizes multiple microprotrusions 4 around the plurality of openings 8 in a redundant way such that all six microprotrusions are coated with electrodes. In this way, if some of the electrodes are damaged during manufacturing, faulty, or do not penetrate the skin, the control unit 10 can test at start up to see which electrodes are working and only utilize the working electrodes for detecting the agent. Likewise, more than one set of microprotrusions and openings can be located on a member 2 as shown. Also, as shown in FIG. 4, two sets of three electrode sensors are shown around each opening 8 for redundancy and accuracy.

The distal ends of microprotrusions 4 can have any of a variety of shapes and configurations for piercing the skin or body surface, including arrow-shaped or diamond-shaped ends as shown in FIGS. 1 and 2, triangular-shaped ends as shown in FIG. 4 and pins (not shown). The microprotrusions 4 penetrate the stratum corneum of the epidermis when pressure is applied to the device to facilitate the detecting of an agent through a body surface. The term "body surface" as used herein refers generally to the outermost layer of skin, mucous membranes, and nails of an animal or human, and to the outer surface of a plant.

In the illustrated embodiment, the plate 6 is formed with an opening 8 between the microprotrusions 4. The opening 8 corresponds to the portion of the plate 6 occupied by each of the microprotrusions 4 prior to the microprotrusions being bent into a position which is substantially perpendicular to the plane of plate 6. The number of openings 8 per device and the number of microprotrusions 4 per device are independent. The device may have only one large opening 8 with a plurality of microprotrusions 4 around the opening. As will be described below, the opening 8 may be covered with a fluid-attracting member for enhancing the movement of an agent being sampled past the electrodes and into a fluid-attracting reservoir. In another embodiment, the device does not have an opening 8 through the plate 6. In this latter embodiment, the microprotrusions 4 are made by molding or casting and are then coated with the electrodes.

The microprotrusions 4 are generally formed from a single piece of material (although they need not be) and are sufficiently sharp and long for puncturing at least the stratum corneum of the body surface. In one embodiment, the microprotrusions 4 and the plate 6 are essentially impermeable or are impermeable to the passage of an agent. The width of each microprotrusion can be any of a range of widths. Usually, the width of the microprotrusion is in the range of about 25 micrometers to 500 micrometers. The length of the microprotrusions is subject to variation of the body surface being penetrated and corresponds to the natural thickness of the stratum corneum for one of the features of the invention is that the sensor electrode detects the agent below the outermost layer of the epidermis. Usually, the microprotrusions will be about 20 micrometers to about 400 micrometers in length. The microprotrusions 4 can have slanted (i.e., angled) leading edges 64 (FIG. 4) to further reduce the insertion force required to press the microprotrusions into the body surface. The leading edges of each microprotrusion can be all the same angle or can be at different angles suitable for piercing the body surface. Alternatively, the leading edge of each microprotrusion can be arcuate (i.e., curved) in shape, having, for example, a convex or concave shape.

The member 2 can also improve the attachment of the device to the body surface so that continuous agent detection through the body surface is preserved during movement of the body surface. In the embodiment shown in FIG. 4, projections in the form of barbs 50 on at least one of the microprotrusions 4 assist in anchoring the member 2 and any corresponding device or structure used in combination therewith to the body surface. Barbs 50 can be on any number of the microprotrusions from one to all microprotrusions. The barbs 50 are optional as other means for holding the member in contact with the body surface can be used. The present invention can be used in conjunction with a wide variety of microprotrusions configurations, for example, reference may be had to U.S. Provisional Application No. 60/019,990 filed Jun. 18, 1996 of which any of the disclosed configurations can be used with the present invention.

The pattern for any of the microprotrusion array members 2 of the present invention can be produced with a photo-etching process. For example, reference may be had to U.S. Provisional Application No. 60/019,990 filed Jun. 18, 1996 of which any of the disclosed methods can be used to produce the member 2 of the present invention. A thin plate 6 of metal such as stainless steel or titanium is etched photo-lithographically with patterns containing skin piercing structures. In general, a thin laminate dry resist or wet resist is applied on the plate 6 which typically has a thickness of about 7 micrometers to about 100 micrometers, preferably about 25 micrometers to about 50 micrometers. The resist is contact exposed using a mask having the desired pattern and is subsequently developed. These operations are conducted in much the same way that they are for the manufacture of a printed circuit board. The plate 6 is then etched using acidic solutions. After the pattern has been etched through the plate, the plate 6 is placed on a die having a plurality of openings corresponding to the openings 8 in the plate. A punch having a plurality of protrusions corresponding to the openings 8 in the plate 6 and openings in the die is initially located above the plate and the die. At the initial stage, the microprotrusions 4 are in the same plane as the rest of the plate 6. The punch dies are then pressed into the openings 8, thus bending the microprotrusions downward to be substantially perpendicular to the plane of the plate 6. The finished structure provides microprotrusions 4 with an adjacent opening 8. In one embodiment, the opening 8 allows the passage of interstitial fluid therethrough when the member 2 is applied to the body surface. Rectangular openings 8 are shown in the figures but the invention encompasses the use of any shape openings including, but not limited to, square, triangular, circular and elliptical.

Generally, the microprotrusions 4 are at an angle of about 90 degrees to the surface 48 (FIG. 3) of the plate 6 after being punched, but they can be disposed at any angle forward or backward from the perpendicular position that will facilitate penetration of and attachment to the body surface. In addition, other anchoring elements such as barbs, openings, etc. can be used with the angled microprotrusions to further enhance anchoring of the device.

The plates 6 and microprotrusions 4 can be made from materials that have sufficient strength and manufacturability to produce microprotrusions, such as, glasses, ceramics, rigid polymers, metals and metal alloys. Examples of metals and metal alloys include but are not limited to stainless steel, iron, steel, tin, zinc, copper, silver, platinum, aluminum, germanium, nickel, zirconium, titanium and titanium alloys having nickel, molybdenum or chromium. Each of the plate and microprotrusions can have a thin layer of silver, gold, platinum, iridium, titanium, rhodium plating or evaporated or sputtered biocompatible metals to provide for inertness, biocompatibility and preservation of the sharpness of the edges during storage. An example of glasses include a devitrified glass such as "PHOTOCERAM" available from Corning in Corning, N.Y. Examples of polymers include but are not limited to polystyrene, polymethylmethacrylate, polypropylene, "BAKELITE", cellulose acetate, ethyl cellulose, styrene/acrylonitrile copolymers, styrene/butadiene copolymers, acrylonitrile/butadiene/styrene (ABS) copolymers, polyvinyl chloride and acrylic acid polymers including polyacrylates and polymethacrylates.

The number of microprotrusions 4 and electrodes of any of the embodiments of the member 2 is variable with respect to the redundancy desired in the system, the agent being detected, the type of sensor being used, and other factors as will be evident to one of ordinary skill in the art.

The member 2 can optionally be made to adhere to the patient's body surface by various means, including an adhesive applied to the body-contacting side of plate 6 or other anchoring elements on the member 2 of any of the embodiments discussed herein. Further, a watch band or elastic bandage can be used to maintain the device in contact with the skin. The adhesive should have sufficient tack to insure that the member 2 remains in place on the body surface during normal user activity, and yet permits reasonable removal after the predetermined (e.g., 24-hour) wear period. A suitable release liner (not shown) is preferably provided for maintaining the integrity of the adhesive before use. In use, the release liner is stripped from the adhesive before the device is applied to the skin.

Figure 5:
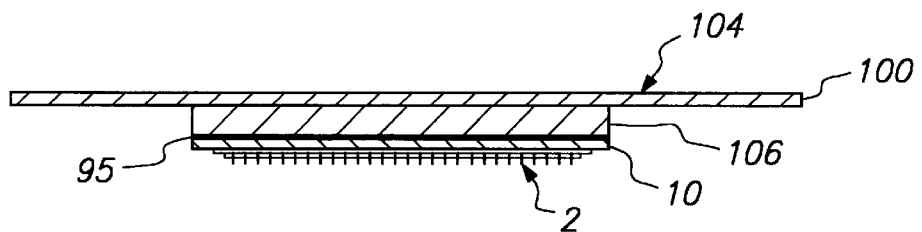
FIG. 5 is a diagrammatic cross-sectional view of an osmotic detecting device in accordance with the present invention.

As mentioned, the member 2 of the present invention can also be used with fluid-attracting regimes including, but not limited to, reverse electrotransport (i.e., iontophoresis and/or electroosmosis), osmosis, and passive diffusion. FIG. 5 illustrates an osmotic device 104 in combination with any of the embodiments described previously for member 2. Osmotic devices can be used to draw fluid from the body (i.e., interstitial fluid or sweat) which carries the agent to be detected, for example, reference may be had to U.S. Pat. No. 4,756,314 of which the disclosed osmotic configurations can be used with the present invention. The osmotic device 104 is attached to a body surface by means of a flexible adhesive overlay 100. Device 104 is comprised of a salt layer 106 separated by semi-permeable membrane 95 from control unit or detector 10 and member 2. The salt layer 106 draws fluid from the patient's body by osmosis. The fluid drawn from the body contains the agent being detected. In this way, with the electrodes located at the distal ends of the microprotrusions, a constant flow of interstitial fluid can be maintained past the electrodes and through the openings 8. Preferably, the salt layer 106 is free to expand or is encapsulated in a semi-permeable membrane 95 so that it retains the fluid therein. With this configuration, the agent is detected in situ below the body surface as the interstitial fluid flows past the electrodes. Alternatively, salt layer 106 and semi-permeable membrane 95 can be combined in one layer of absorbent hydrogel that stores the absorbed fluid as well as the agent.

It will be appreciated by those of ordinary skill in the art that the invention can be embodied in other specific forms without departing from the spirit or essential character thereof. The presently disclosed embodiments are therefore considered in all respects to be illustrative and not restrictive. The scope of the invention is indicated by the appended claims rather than the foregoing description, and all changes which come within the meaning and range of equivalents thereof are intended to be embraced therein.

What is claimed is:

1. A detecting device, comprising:
   a plate having at least one microprotrusion fixedly attached to the plate and extending therefrom; and
   an agent-detecting sensor on the microprotrusion, the microprotrusion having a length which locates the sensor below the outermost layer of a body surface and in contact with a body fluid.

2. The detecting device of claim 1 further comprising:
   a detector and wherein the sensor is an electrochemical sensor having a proximal segment attached to the detector and a distal segment having at least one electrode thereon.

3. The detecting device of claim 1 wherein the microprotrusion locates the sensor just below the outermost layer of the epidermis above the nerve endings and blood vessels of a patient.

4. The detecting device of claim 1 wherein the sensor is a thin film sensor.

5. The device of claim 4, wherein the sensor comprises a coating on the microprotrusion.

6. The detecting device of claim 1 wherein the sensor is a glucose sensor.

7. The detecting device of claim 1 wherein the sensor is located on two sides of the microprotrusion.

8. The detecting device of claim 1 wherein the device further comprises means for anchoring the device in the body surface.

9. The detecting device of claim 1 wherein the plate has an opening therethrough in communication with a fluid-attracting member.

10. The detecting device of claim 9 wherein the fluid-attracting member is an osmotic salt layer.

11. The device of claim 1, wherein the microprotrusion is an integral part of the plate.

12. The device of claim 11, wherein the body fluid is interstitial fluid.

13. A device for detecting an agent below an outermost layer of epidermis of a patient, comprising:
   at least one electrochemical sensor; and
   a plurality of skin-piercing microprotrusions fixedly attached to the device, each of the microprotrusions having an electrode of the electrochemical sensor thereon, the microprotrusions having a length, which locates the electrodes below the outermost layer of the epidermis and in contact with a body fluid.

14. The device of claim 13 wherein the skin-piercing microprotrusions locate the sensor just below the outermost layer of the epidermis above the nerve endings and blood vessels of the patient.

15. The device of claim 13 wherein one of the microprotrusions is a sample electrode, one of the microprotrusions is a common electrode, and one of the microprotrusions is a reference electrode.

16. The device of claim 13, further comprising electrical traces extending from each of the electrodes to interface with a detector.

17. The device of claim 13 wherein each microprotrusion has an enlarged electrode surface at its distal end.

18. The device of claim 13 wherein each microprotrusion has a diamond-shaped electrode surface at its distal end.

19. The device of claim 13 wherein the device has an opening therethrough in communication with a fluid-attracting member.

20. The device of claim 19 wherein the fluid-attracting member is an osmotic salt layer.

21. The device of claim 13 wherein the electrode of each of the microprotrusions is located on two sides of the microprotrusion.

22. The device of claim 13 wherein the electrochemical sensor is a glucose sensor.

23. A method for detecting an agent in a patient, comprising:

placing a plate against the patient's skin, the plate having at least one microprotrusion fixedly attached to the plate and extending therefrom to pierce the skin when the plate is placed thereon, the microprotrusion having a sensor thereon to detect the agent, the microprotrusion having a length which locates the sensor below an outermost layer of epidermis of the patient and in contact with a body fluid; and detecting the agent.

24. The method of claim 23 further comprising:

locating the sensor just below the outermost layer of the epidermis above the nerve endings and blood vessels of the patient.

25. The method of claim 23 further comprising:

withdrawing fluid from the patient's skin with the detecting device to produce a flow of fluid past the sensor.

26. The method of claim 23 wherein the detecting step is performed periodically.

27. The method of claim 23, wherein the microprotrusion is an integral part of the device.

28. The method of claim 27, wherein the body fluid is interstitial fluid.

29. The method of claim 23, wherein the sensor comprises a coating on the microprotrusion.

* * * * *